United States Patent [19]

Wurst

[11] Patent Number: 5,976,842
[45] Date of Patent: Nov. 2, 1999

[54] METHODS AND COMPOSITIONS FOR USE IN HIGH FIDELITY POLYMERASE CHAIN REACTION

[75] Inventor: Helmut Wurst, Palo Alto, Calif.

[73] Assignee: Clontech Laboratories, Inc., Palo Alto, Calif.

[21] Appl. No.: 08/960,718

[22] Filed: Oct. 30, 1997

[51] Int. Cl.$^6$ .............. C12P 19/34; C12Q 1/68; C07H 21/00; C07H 21/02
[52] U.S. Cl. .............. 435/91.2; 435/6; 435/91.1; 435/188; 435/194; 536/23.1; 536/24.33
[58] Field of Search .............. 435/91.1, 91.2, 435/188, 194, 6; 536/23.1

[56] References Cited

U.S. PATENT DOCUMENTS

| | | | |
|---|---|---|---|
| 5,436,149 | 7/1995 | Barnes | 435/194 |
| 5,491,086 | 2/1996 | Gelfand et al. | 435/194 |
| 5,512,462 | 4/1996 | Cheng | 435/91.2 |

OTHER PUBLICATIONS

Barnes et al Proc. Natl. Acad. Sci. USA vol. 91, pp. 2216–2220, 1994.
Eckert et al Nucleic Acids Research vol. 18. No. 13 pp. 3739–3743, 1990.
Vartanian et al Nucleic Acids Research vol. 24, No. 14 pp. 2627–2631, 1996.
Varadaraj et al Gene vol. 140 pp. 1–5, 1994.
Gelfand PCR Technology Principles and Aplications for DNA Amplification Stockton Press NY pp. 17–22, 1989.
Cheng et al Proc. Natl. Acad. Sci. USA vol. 91, pp. 5695–5699, 1994.
Taylor, Graham et al., "The Polymerase Chain Reaction: New Variations On An Old Theme," *Current Opinion In Biotechnology* (1995) vol. 6:24–29.
Varadaraj, Kulandaiappan et al., "Denaturants or Cosolvents Improve the Specificity of PCR Amplification of a G+C–rich DNA Using Genetically Engineered DNA Polymerases," *Gene* (1994) vol. 140:1–5.

Vartanian, Jean–Pierre et al., "Hypermutagenic PCR Involving All Four Transitions and a Sizeable Proportion of Transversions," *Nucleic Acids Research* (1996) vol. 24, (14):2627–2631.
Fromant, Michel et al., "Direct Random Mutagenesis of Gene–Sized DNA Fragments Using Polymerase Chain reaction," *Analytical Biochemistry* (1995) vol. 224:347–353.
Braithwaite, Dan et al., "Compilation, Alignment, and Phylogenetic Relationships of DNA Polymerases," *Nucleic Acids Research* (1993) vol. 21, (4):787–802.
Barnes, Wayne M., "PCR Amplificaton of up to 35–kb DNA With High Fidelity and High yield From λ Bacteriophage templates," *Proc. Natl. Acad. Sci. USA* (1994) vol. 91:2216–2220.
Eckert, Kristin et al., "DNA Polymerase Fidelity and the Polymerase Chain Reaction," *Cold Spring Harbor Laboratory Press* (1991) pp. 17–24, PCR Methods and Applications.
Eckert, Kristin et al., "High Fidelity DNA Synthesis by the *Thermus aquatics* DNA Polymerase," *Nucleic Acids Research* (1990) vol. 18, (13):3739–3743.
Ling, Lucy et al., "Optimization of the polymerase Chain Reaction with Regard to Fidelity: Modified T7, Taq, and Vent DNA Polymerases," *Cold Spring Harbor Laboratory Press* (1991) pp. 63–69, PCR Methods and Applications.

*Primary Examiner*—Kenneth R. Horlick
*Assistant Examiner*—Jeffrey Siew
*Attorney, Agent, or Firm*—Bozicevic, Field & Francis LLP; Bret Field

[57] ABSTRACT

Methods and compositions are provided for performing high fidelity polymerase chain reactions. In the subject methods, primer extension products are produced with a low error frequency rate through the use of at least one of unequal concentrations of dNTPs or a melting point reducing agent. Also provided are kits and reagent mixtures for use in the subject methods. The subject invention finds use in a variety of applications, particularly in applications where high fidelity PCR is desired.

29 Claims, 1 Drawing Sheet

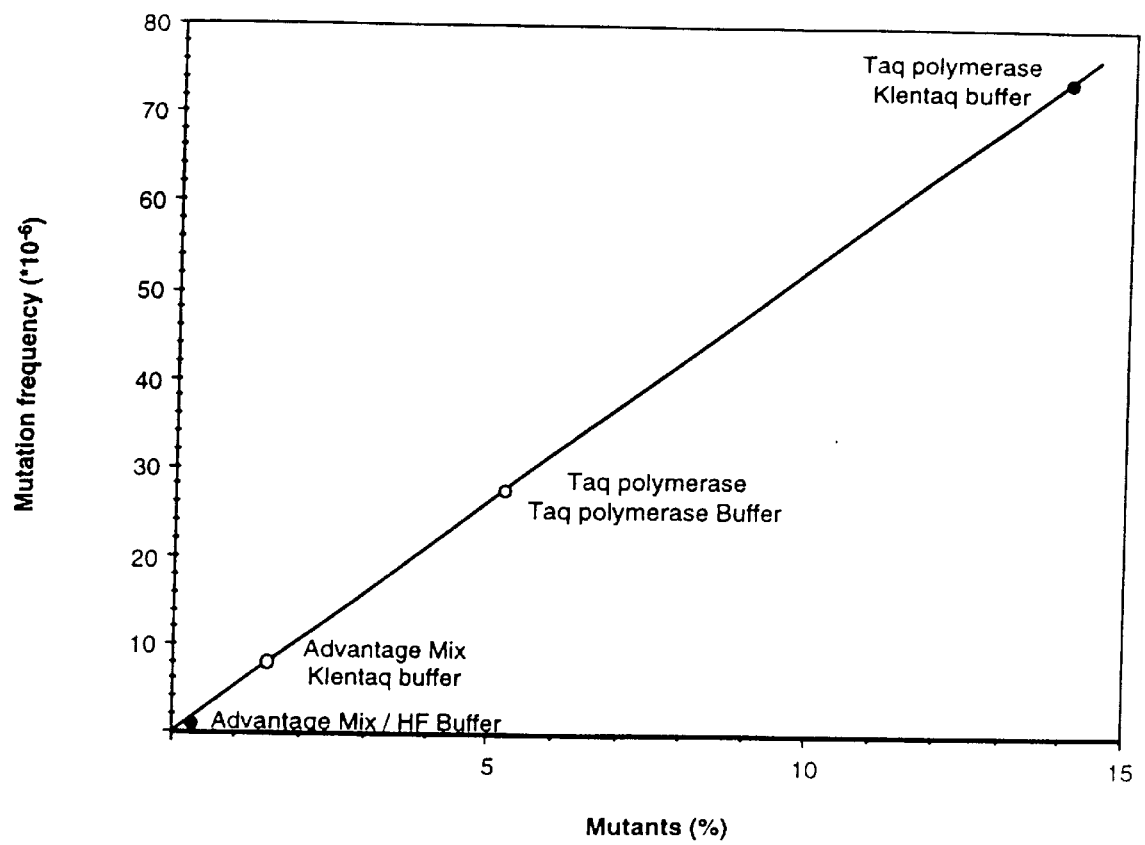

5,976,842

SEQUENCE LISTING

```
<160> NUMBER OF SEQ ID NOS: 2

<210> SEQ ID NO 1
<211> LENGTH: 29
<212> TYPE: DNA
<213> ORGANISM: Artificial Sequence
<220> FEATURE:
<223> OTHER INFORMATION: primer

<400> SEQUENCE: 1
aaaaacgcgt caccagtcac agaaaagca                                    29

<210> SEQ ID NO 2
<211> LENGTH: 34
<212> TYPE: DNA
<213> ORGANISM: Artificial Sequence
<220> FEATURE:
<223> OTHER INFORMATION: primer

<400> SEQUENCE: 2
aaaaacgcgt caaccaagtc attctgagaa tagt                              34
```

METHODS AND COMPOSITIONS FOR USE IN HIGH FIDELITY POLYMERASE CHAIN REACTION

TECHNICAL FIELD

The field of this invention is the polymerase chain reaction.

BACKGROUND OF THE INVENTION

The polymerase chain reaction (PCR) is a method that is finding ever increasing use in the molecular biology and fields related thereto. The method of PCR was first described in the mid-1980s. See Mullis et al., Cold Spring Harbor Symp. Quant. Biol. (1986) 51:263, Saiki et al., Science (1985) 230:1350; and Mullis & Faloona, Methods Enzymol. (1987) 155:335. PCR finds use in a variety of applications, including the generation of probes for DNA of both known and unknown nucleic acid sequences, the generation of cDNA libraries, DNA sequencing, analysis of mutations, chromosome crawling, and the like.

Generally, PCR results in the amplification of a segment of DNA that lies between two regions of known sequence. In PCR, two oligonucleotides are used as primers for a series of synthetic reactions that are enzymatically catalyzed by a DNA polymerase. The primers are complementary to regions on opposite strands of the DNA and flank the region of DNA to be amplified. The template DNA is first denatured by heating the DNA in the presence of an excess of primer and the dNTPs. The mixture is then cooled to provide for primer annealing and extension. The cycle of denaturation, annealing and synthesis is repeated a plurality of times, which results in the production of an amplified amount of template DNA.

One limitation of PCR methods is a lack of fidelity, i.e. misincorporation of base pairs during the synthesis step. While for certain applications mispairing of bases may not pose a serious problem, for other applications low fidelity renders PCR practically useless. While methods have been developed which provide for improved fidelity, such improvements typically are concomitant with a decrease in efficiency.

Thus, there is a continued need for the development of improved methods of PCR, where the development of PCR methods which provide both high fidelity and efficiency is of particular interest.

Relevant Literature

The polymerase chain reaction is reviewed in Sambrook, Fritsch & Maniatis, Molecular Cloning: A Laboratory Manual (Cold Spring Harbor Laboratory Press, 1989) Chapter 14. Other references reviewing PCR include: Ling et al., PCR Methods and Applications (1991) 63–69; Eckert & Kunkel, Nuc. Acids Res. (1990) 18:3739 and Eckert & Kunkel, PCR Methods and Applications (1991) 63–39.

Braithewaite & Ito, Nuc. Acids Res. (1993) 21:787–802 provide a review of known DNA polymerases.

Barnes, Proc. Natl. Acad. Sci. USA (1994) 91:2216–2220 reports the results of using a combination of Klentaq and Pfu polymerases in PCR amplification.

SUMMARY OF THE INVENTION

Methods and compositions are provided for performing high fidelity polymerase chain reactions. In the subject methods, target nucleic acid is contacted with a polymerase chain reaction reagent mixture under reaction conditions sufficient to enzymatically produce primer extension product with a low error frequency rate. In the subject methods, the reaction conditions are characterized by the presence at least one of: (a) unequal concentrations of dNTPs and (b) a melting point reducing agent. Also provided are novel reagent mixtures and kits for use in the subject methods. The subject methods find use in applications where the polymerase chain reaction is performed, particularly in those applications where high fidelity is desired.

BRIEF DESCRIPTION OF THE FIGURES

FIG. 1: Standardization of Fidelity Assay—The data of Table 6 are represented in closed circles (•). Open circles (o) represent PCR systems with known fidelity in the Fidelity Assay but lacking sequencing data.

DESCRIPTION OF THE SPECIFIC EMBODIMENTS

Methods and compositions are provided for performing high fidelity polymerase chain reactions. In the subject methods, target DNA is contacted with a polymerase chain reaction (PCR) reagent mixture under reaction conditions sufficient to enzymatically produce primer extension product with a low error frequency rate. In the subject methods, the reaction conditions are characterized by the presence of at least one of: (a) unequal concentrations of dNTPs and (b) a melting point reducing agent. Also provided are the reagent mixtures and kits for use in the subject methods. The subject invention finds use in applications in which PCR is performed, particularly in situations where high fidelity PCR is desired.

Before the subject invention is further described, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

It must be noted that as used in this specification and the appended claims, the singular forms "a," "an," and "the" include plural reference unless the context clearly dictates otherwise. Unless defined otherwise all technical and scientific terms used herein have the same meaning as commonly understood to one of ordinary skill in the art to which this invention belongs.

The subject invention provides methods of enzymatically producing primer extension products, e.g. in PCR applications, from template nucleic with at least one bacterial polymerase with a low error frequency rate, whereby low error frequency rate is meant an error frequency rate at or below (i.e. not in excess of) $4 \times 10^{-6}$, preferably at or below $2 \times 10^{-6}$, and more preferably at or below $1.3 \times 10^{-6}$ mutations per base pair per PCR cycle.

The polymerase chain reaction (PCR) in which nucleic acid primer extension product is enzymatically produced from template DNA are well known in the art, being described in U.S. Pat. Nos.: 4,683,202; 4,683,195; 4,800,159; 4,965,188 and 5,512,462, the disclosures of which are herein incorporated by reference.

In the subject methods, template nucleic acid is first contacted with primer and polymerase under conditions sufficient to enzymatically produce primer extension product. The nucleic acid that serves as template may be single stranded or double stranded, where the nucleic is typically deoxyribonucleic acid (DNA), where when the nucleic acid is single stranded, it will typically be converted to double stranded nucleic acid using one of a variety of methods known in the art. The length of the template nucleic acid may be as short as 50 bp, but usually be at least about 100 bp long, and more usually at least about 150 bp long, and may be as long as 10,000 bp or longer, but will usually not exceed 50,000 bp in length, and more usually will not exceed 20,000 bp in length. The nucleic acid may be free in solution, flanked at one or both ends with non-template nucleic acid, present in a vector, e.g. plasmid and the like, with the only criteria being that the nucleic acid be available for participation in the primer extension reaction. The template nucleic acid may be derived from a variety of different sources, depending on the application for which the PCR is being performed, where such sources include organisms that comprise nucleic acids, i.e. viruses; prokaryotes, e.g. bacteria, archaea and cyanobacteria; and eukaryotes, e.g. members of the kingdom protista, such as flagellates, amoebas and their relatives, amoeboid parasites, ciliates and the like; members of the kingdom fungi, such as slime molds, acellular slime molds, cellular slime molds, water molds, true molds, conjugating fungi, sac fungi, club fungi, imperfect fungi and the like; plants, such as algae, mosses, liverworts, hornworts, club mosses, horsetails, ferns, gymnosperms and flowering plants, both monocots and dicots; and animals, including sponges, members of the phylum cnidaria, e.g jelly fish, corals and the like, combjellies, worms, rotifers, roundworms, annelids, molluscs, arthropods, echinoderms, acorn worms, and vertebrates, including reptiles, fishes, birds, snakes, and mammals, e.g. rodents, primates, including humans, and the like. The nucleic acid may be used directly from its naturally occurring source and/or preprocessed in a number of different ways, as is known in the art. In some embodiments, the nucleic acid may be from a synthetic source.

As mentioned above, the template nucleic acid is contacted with primer, polymerase and other reagents into a reaction mixture. The amount of template nucleic acid that is combined with the other reagents will range from about 1 molecule to 1 pmol, usually from about 50 molecules to 0.1 pmol, and more usually from about 0.01 pmol to 100 fmol.

The oligonucleotide primers with which the template nucleic acid (hereinafter referred to as template DNA for convenience) is contacted will be of sufficient length to provide for hybridization to complementary template DNA under annealing conditions (described in greater detail below) but will be of insufficient length to form stable hybrids with template DNA under polymerization conditions. The primers will generally be at least 10 bp in length, usually at least 15 bp in length and more usually at least 16 bp in length and may be as long as 30 bp in length or longer, where the length of the primers will generally range from 18 to 50 bp in length, usually from about 20 to 35 bp in length. The template DNA may be contacted with a single primer or a set of two primers, depending on whether linear or exponential amplification of the template DNA is desired. Where a single primer is employed, the primer will typically be complementary to one of the 3' ends of the template DNA and when two primers are employed, the primers will typically be complementary to the two 3' ends of the double stranded template DNA.

The subject methods employ at least one Family A polymerase, and in many embodiments a combination of two or more different polymerases, usually two, different polymerases. The polymerases employed will typically, though not necessarily, be thermostable polymerases. The polymerase combination with which the template DNA and primer is contacted will comprise at least one Family A polymerase and, in many embodiments, a Family A polymerase and a Family B polymerase, where the terms "Family A" and "Family B" correspond to the classification scheme reported in Braithwaite & Ito, Nucleic Acids Res. (1993) 21:787–802. Family A polymerases of interest include: *Thermus aquaticus* polymerases, including the naturally occurring polymerase (Taq) and derivatives and homologues thereof, such as Klentaq (as described in Proc. Natl. Acad. Sci USA (1994) 91:2216–2220); *Thermus thermophilus* polymerases, including the naturally occurring polymerase (Tth) and derivatives and homologues thereof, and the like. Family B polymerases of interest include *Thermococcus litoralis* DNA polymerase (Vent) as described in Perler et al., Proc. Natl. Acad. Sci. USA (1992) 89:5577; Pyrococcus species GB-D (Deep Vent); *Pyrococcus furiosus* DNA polymerase (Pfu) as described in Lundberg et al., Gene (1991) 108:1–6, *Pyrococcus woesei* (Pwo) and the like. Of the two types of polymerases employed, the Family A polymerase will be present in an amount greater than the Family B polymerase, where the difference in activity will usually be at least 10-fold, and more usually at least about 100-fold. Accordingly, the reaction mixture prepared upon contact of the template DNA, primer, polymerase and other necessary reagents, as described in greater detail below, will typically comprise from about 0.1 U/$\mu$l to 1 U/$\mu$l Family A polymerase, usually from about 0.2 to 0.5 U/$\mu$l Family A polymerase, while the amount of Family B polymerase will typically range from about 0.01 mU/$\mu$l to 10 mU/$\mu$l, usually from about 0.05 to 1 mU/$\mu$l and more usually from about 0.1 to 0.5 mU/$\mu$l, where "U" corresponds to incorporation of 10 nmol dNTP into acid-insoluble material in 30 min at 74° C. In a preferred embodiment, the Family A polymerase is Klentaq while the Family B polymerase is Deep Vent, where the ratio of activity of Klentaq to Deep Vent will range from 50 to 10,000, more usually from 500 to 1000.

In the subject invention, unequal amounts of deoxyribonucleoside triphosphates (dNTPs) are employed. By unequal amounts is meant that at least one of the different types of dNTPs is present in the reaction mixture in an amount that differs from the amount at which the other dNTPs are present, i.e. a unique amount. The amount of difference will be at least about 1.5 and usually at least about 2. Usually the reaction mixture will comprise four different types of dNTPs corresponding to the four naturally occurring bases are present, i.e. dATP, dTTP, dCTP and dGTP. Where the dNTPs employed are dATP, dTTP, dCTP and dGTP, only one of the dNTPs may be present at a unique amount, two of the dNTPs may be present at unique amounts, or all of the dNTPs may be present at unique amounts. In one preferred embodiment, dATP is present in a concentration greater than the individual concentrations of the remaining three dNTPs, i.e. dGTP, dCTP & dTTP. In another preferred embodiment, dGTP is present in a lower concentration than the individual concentrations of the remaining three dNTPs. In the subject methods, dATP will typically be present in an amount ranging from about 250 to 5000 $\mu$M, usually from about 300 to 1000 $\mu$M; dTTP will typically be present in an amount ranging from about 50 to 5000 $\mu$M, usually from about 100 to 400 $\mu$M; dCTP will typically be present in an amount ranging from about 50 to 5000 $\mu$M, usually from about 100 to 400 $\mu$M; and dGTP will typically be present in an amount ranging from about 10 to 150 $\mu$M, usually from about 20 to 100 $\mu$M.

Also present in the reaction mixtures of certain preferred embodiments of the subject invention is a melting point reducing agent, i.e. a reagent that reduces the melting point of DNA (or base-pair destabilization agent). Suitable melting point reducing agents are those agents that interfere with the hydrogen bonding interaction of two nucleotides, where representative base pair destabilization agents include: formamide, urea, thiourea, acetamide, methylurea, glycinamide, and the like, where urea is a preferred agent. The melting point reducing agent will typically be present in amounts ranging from about 20 to 500 mM, usually from about 50 to 200 mM and more usually from about 80 to 150 mM.

The reaction mixture will further comprise an aqueous buffer medium which includes a source of monovalent ions, a source of divalent cations and a buffering agent. Any convenient source of monovalent ions, such as KCl, K-acetate, $NH_4$-acetate, K-glutamate, $NH_4Cl$, ammonium sulfate, and the like may be employed, where the amount of monovalent ion source present in the buffer will typically be present in an amount sufficient to provide for a conductivity in a range from about 500 to 20,000, usually from about 1000 to 10,000, and more usually from about 3,000 to 6,000 micromhos. The divalent cation may be magnesium, manganese, zinc and the like, where the cation will typically be magnesium. Any convenient source of magnesium cation may be employed, including $MgCl_2$, Mg-acetate, and the like. The amount of $Mg^{2-}$ present in the buffer may range from 0.5 to 10 mM, but will preferably range from about 2 to 4 mM, more preferably from about 2.25 to 2.75 mM and will ideally be at about 2.45 mM. Representative buffering agents or salts that may be present in the buffer include Tris, Tricine, HEPES, MOPS and the like, where the amount of buffering agent will typically range from about 5 to 150 mM, usually from about 10 to 100 mM, and more usually from about 20 to 50 mM, where in certain preferred embodiments the buffering agent will be present in an amount sufficient to provide a pH ranging from about 6.0 to 9.5, where most preferred is pH 7.3 at 72° C. Other agents which may be present in the buffer medium include chelating agents, such as EDTA, EGTA and the like.

In preparing the reaction mixture, the various constituent components may be combined in any convenient order. For example, the buffer may be combined with primer, polymerase and then template DNA, or all of the various constituent components may be combined at the same time to produce the reaction mixture.

Following preparation of the reaction mixture, the reaction mixture is subjected to a plurality of reaction cycles, where each reaction cycle comprises: (1) a denaturation step, (2) an annealing step, and (3) a polymerization step. The number of reaction cycles will vary depending on the application being performed, but will usually be at least 15, more usually at least 20 and may be as high as 60 or higher, where the number of different cycles will typically range from about 20 to 40. For methods where more than about 25, usually more than about 30 cycles are performed, it may be convenient or desirable to introduce additional polymerase into the reaction mixture such that conditions suitable for enzymatic primer extension are maintained.

The denaturation step comprises heating the reaction mixture to an elevated temperature and maintaining the mixture at the elevated temperature for a period of time sufficient for any double stranded or hybridized nucleic acid present in the reaction mixture to dissociate. For denaturation, the temperature of the reaction mixture will usually be raised to, and maintained at, a temperature ranging from about 85 to 100, usually from about 90 to 98 and more usually from about 93 to 96° C. for a period of time ranging from about 3 to 120 sec, usually from about 5 to 30 sec.

Following denaturation, the reaction mixture will be subjected to conditions sufficient for primer annealing to template DNA present in the mixture. The temperature to which the reaction mixture is lowered to achieve these conditions will usually be chosen to provide optimal efficiency and specificity, and will generally range from about 50 to 75, usually from about 55 to 70 and more usually from about 60 to 68° C. Annealing conditions will be maintained for a period of time ranging from about 15 sec to 30 min, usually from about 30 sec to 5 min.

Following annealing of primer to template DNA or during annealing of primer to template DNA, the reaction mixture will be subjected to conditions sufficient to provide for polymerization of nucleotides to the primer ends in manner such that the primer is extended in a 5' to 3' direction using the DNA to which it is hybridized as a template, i.e. conditions sufficient for enzymatic production of primer extension product. To achieve polymerization conditions, the temperature of the reaction mixture will typically be raised to or maintained at a temperature ranging from about 65 to 75, usually from about 67 to 73° C. and maintained for a period of time ranging from about 15 sec to 20 min, usually from about 30 sec to 5 min.

The above cycles of denaturation, annealing and polymerization may be performed using an automated device, typically known as a thermal cycler. Thermal cyclers that may be employed are described in U.S. Pat. Nos. 5,612,473; 5,602,756; 5,538,871; and 5,475,610, the disclosures of which are herein incorporated by reference.

The subject polymerase chain reaction methods find use in any application where the production of enzymatically produced primer extension product from template DNA is desired, such as in the generation of specific sequences of cloned double-stranded DNA for use as probes, the generation of probes specific for uncloned genes by selective amplification of particular segments of cDNA or genomic DNA, the generation of libraries of cDNA from small amounts of mRNA, the generation of large amounts of DNA for sequencing, the analysis of mutations, generation of DNA fragments for gene expression, chromosome crawling, and the like. Thus, the subject methods of PCR find use in diagnosis, such as of genetic disorders and identification of pathogens; in genetic identification of forensic samples, in the analysis of mutations, and the like. The subject methods find particular use in applications where high fidelity PCR is desired.

Also provided are kits for practicing the subject high fidelity PCR methods. The kits according to the present invention will comprise a polymerase and at least one of: (a) unequal amounts of dNTPs and (b) urea, where the polymerase may be a single Family A polymerase or a combination of two or more different polymerases, e.g. a combination of Family A polymerase and a Family B polymerase, as described above, where the various reagent members of the kits may be separated into different containers in the kit or combined into a reagent mixture, where the amount of each polymerase provided may conveniently be the amount employed in the reaction, e.g. more Family A polymerase than Family B polymerase. The subject kits may further comprise additional reagents which are required for or convenient and/or desirable to include in the reaction mixture prepared during the subject methods, where such reagents include an aqueous buffer medium (either prepared or present in its constituent components, where one or more of the components may be premixed or all of the components may be separate), and the like. The various reagent components of the kits may be present in separated containers, or may all be precombined into a reagent mixture for combination with template DNA. The subject kits may further comprise a set of instructions for practicing the subject methods.

The following examples are offered by way of illustration and not by way of limitation.

EXPERIMENTAL

A. Methods

1. PCR:

A plasmid (pMOL21), linearized with ScaI, was used as a template for PCR. The two primers for PCR in the Fidelity Assay were PCRF1 (5'-AAAAACGCGTCACCAGTCACAGAAAAGCA-3') (SEQ ID NO:01) and PCRF2 (5'-AAAAACGCGTCAACCAAGTCATTCTGAGAATAGT-3') (SEQ ID NO:02). PCR was performed in a total volume of 50 µl with 10 pmol of each primer, 1 ng of linearized plasmid DNA, 1 µl of a polymerase system and different buffer conditions and nucleotide concentrations as described in the Results section. PCR was performed in a PCR machine (PTC200) from MJ Research (Watertown, Mass.) at 30 sec at 94° C., then 25 cycles of 15 sec at 94° C. and 3–5 min at 68° C., and finally 3–5 min at 68° C.

2. Buffer Conditions:

Unless otherwise noted, the concentration during PCR of each nucleotide was 200 µM. Klentaq buffer consists of 40 mM K-Tricine (pH 9.2), 15 mM K-acetate, 3.5 mM Mg-acetate, and 75 µg/ml bovine serum albumin. Amplitaq Buffer contains 10 mM Tris-HCl (pH 8.3), 50 mM KCl, 1.5 mM MgCl$_2$, 10 µg/ml gelatin. The HF Buffer consisted of 40 mM K-Tricine (pH 8.2), 25 mM K-acetate, 2.5 mM Mg-acetate, 100 µg/ml bovine serum albumin, 100 mM urea, 0.05 mM EDTA. This buffer was used with 500 µM dATP, 50 µM dGTP, 200 µM dCTP, and 200 µM dTTP. Fidelity at different pH-values was determined by PCR in 40 mM Tricine buffer titrated with with KOH at room temperature, 3.5 mM Mg-acetate, and 75 µg/ml bovine serum albumin. K-acetate was added at various amounts to provide a final conductivity of 3600 Micromho at all pH values. Conductivity was determined at room temperature. The effect of urea was measured using the Klentaq Buffer. The dependence of fidelity on magnesium was measured in a PCR with the Klentaq Buffer system, except that different amounts of magnesium were added separately. The effect on different nucleotide concentrations was also measured using the Klentaq buffer. Amplifications with Taq polymerase (Amplitaq, Perkin-Elmer) were either performed in Amplitaq Buffer or in Klentaq buffer.

3. Measurement of DNA Concentration:

DNA concentration after PCR was measured with a TKO100 fluorometer from Hoefer (San Francisco) using H33258 as a fluorophore (Cesarone, Bolognesi et al. 1979) and lambda DNA as a standard.

4. Fidelity Assay:

An assay as described in Mo & Maki, J. Mol. Biol. (1991) 222:925–936 was employed, where the amount of mutants was determined as the ratio of carbenicillin-resistant transformants and of transformants resistant to both carbenicillin and streptomycin. The percentage of transformants with resistance to both antibiotic markers compared to the number of total transformants then indicates the mutagenicity of the preceding PCR.

B. Results

1. Fidelity at Varying Proton Concentrations

The fidelity of Taq polymerase increases with a decrease in pH (Eckert and Kunkel, Nucleic Acids Research (1990) 18:3739–3744). A similar pattern could be observed with the Advantage cDNA Mix in the rpsL Fidelity Assay (Table 1). However, the efficiency of PCR, as indicated by the DNA concentration after PCR, decreases with the pH, probably caused by lower polymerase activity of the Advantage Mix.

TABLE 1

Fidelity of ADVANTAGE MIX ™ medium at different pH

| pH | rpsL Mutants (%) | DNA concentration (ng/µl) |
| --- | --- | --- |
| 9.2 | 2.6 | 188 |
| 8.7 | 1.7 | 201 |
| 8.2 | 1.4 | 154 |
| 7.7 | 1.4 | 143 |
| 7.2 | 0.8 | 32 |

2. Fidelity in the Presence of Urea

Addition of denaturants, such as urea also increased fidelity (Table 2). This increase in fidelity was again gained with a loss in DNA yield.

TABLE 2

Fidelity in the presence of urea

| Urea (mM) | Mutants (%) | DNA concentration (ng/µl) |
| --- | --- | --- |
| 0 | 1.9 | 183 |
| 100 | 1.0 | 134 |
| 200 | 0.5 | 43 |

3. Effect of Magnesium and Nucleotide Concentrations on Fidelity

It has been shown previously that low magnesium concentrations and low nucleotide concentrations increase fidelity of Taq polymerase (Eckert and Kunkel supra; Ling, Keohavong et al. PCR Methods Appl. (1991) 1:63–69). The same was true for the ADVANTAGE MIX (Tables 3 and 4). It should be noted that for unknown reasons the fidelity in these experiments was lower than usual. Lowering the concentration of magnesium from 3.5 mM to 1.5 mM resulted in a almost 10-fold increase in fidelity, but this gain was accompanied by a 7-fold loss in DNA yield. Lowering the concentration of all four nucleotides by 10-fold resulted in a 9-fold higher fidelity. This was again accompanied by a loss in DNA yield.

We measured fidelity at unequal nucleotide concentrations. As can be seen in Table 4, a higher concentration of dATP compared to the three other nucleotides and a lower concentration of dGTP compared to the three other nucleotides has a positive effect on fidelity. The overall DNA yield increased with the nucleotide concentration. Therefore, increasing dATP relative to the other nucleotides results not only in higher fidelity, but also in higher DNA yield. For the same reason, the increased fidelity from lowering dGTP relative to the other three nucleotides is accompanied by a loss in DNA yield.

TABLE 3

Effect of magnesium on fidelity

| Magnesium (mM) | Mutants (%) | DNA concentration (ng/μl) |
|---|---|---|
| 3.5 | 7.9 | 132 |
| 3.0 | 4.2 | 367 |
| 2.5 | 3.7 | 353 |
| 1.5 | 0.8 | 19 |

TABLE 4

Effect of nucleotide concentrations on fidelity

| dATP (μM) | dGTP (μM) | dCTP (μM) | dTTP (μM) | Mutants (%) | DNA concentration (ng/μl) |
|---|---|---|---|---|---|
| 200 | 200 | 200 | 200 | 7.9 | 132 |
| 100 | 100 | 100 | 100 | 7.2 | 74 |
| 50 | 50 | 50 | 50 | 4.0 | 41 |
| 20 | 20 | 20 | 20 | 0.9 | 23 |
| 500 | 100 | 100 | 100 | 2.6 | 73 |
| 500 | 50 | 50 | 50 | 1.0 | 34 |
| 200 | 20 | 200 | 200 | 1.2 | 63 |

4. Comparison of Different PCR Enzymes and Buffers

The above conditions were combined to create a new buffer system. These new conditions consisted of a new buffer (HF Buffer or HF amplification system) and unequal nucleotide concentrations as described in the Methods section.

Several different PCR systems were compared with regard to fidelity (Table 5). The fidelity of Taq polymerase depended on the buffer used. In Klentaq buffer, its fidelity was almost three-fold lower than in Amplitaq Buffer. This is most likely caused by the lower pH and magnesium concentration in the Amplitaq Buffer. The ADVANTAGE MIX had a 3.5-fold higher fidelity than Taq polymerase, and the introduction of the high fidelity conditions increased the fidelity a further 5-fold. Therefore, compared with Taq polymerase used at the manufacturer's conditions, amplification with the ADVANTAGE MIX at high fidelity conditions was 17-fold higher. Amplification at high fidelity conditions has a 3-fold lower DNA yield than amplification with the Advantage Mix at standard conditions. This yield, however, is still higher than the yield after amplification with Taq polymerase alone.

TABLE 5

Fidelity of different PCR systems

| Enzyme | Buffer | Mutants (%) | DNA concentration (ng/μl) |
|---|---|---|---|
| Taq polymerase | Amplitaq Buffer | 5.2 | 40 |
| Taq polymerase | Klentaq Buffer | 14.0 | 62 |
| Advantage Mix | Klentaq Buffer | 1.5 | 220 |
| Advantage Mix | HF buffer | 0.3 | 65 |

5. Standardization of the Fidelity Assay

The Fidelity Assay was standardized by comparing the percentage of rpsL-resistant mutants with the actual frequency of mutations in one sample. This number was determined by sequencing a representative number of independent clones that were obtained after transformation with PCR-amplified pMOL21 (Table 6). The clones were not selected for streptomycin resistance to ensure a random sample.

TABLE 6

Standardization of Fidelity Assay

| Enzyme | Buffer | Clones sequenced | total DNA (bp) | Mutations | Mutation frequency[1] (* $10^{-6}$) | rpsL Mutants (%) |
|---|---|---|---|---|---|---|
| Taq | Klentaq | 60 | 23262 | 43 | 74 | 14.0 |
| Advantage | HF | 185 | 82391 | 2 | 1 | 0.3 |

[1]: Mutation frequency is expressed as the number of mutations per sequenced base pair per PCR cycle.

A standard curve (FIG. 1) was prepared from the data in Table 6. It was constructed using the assumption that the amount of mutants in the Fidelity Assay is proportional to the number of mutations after PCR. This calibration allowed the determination of the mutation frequency of other PCR systems from the determination of the fidelity in the Fidelity Assay.

Based on this standardization the mutation frequency of Taq polymerase in the appropriate buffer is $2.8*10^{-5}$ and that of the Advantage Mix in Klentaq Buffer is $8*10^{-6}$. The value for Taq polymerase corresponds well with published values (Tindall and Kunkel, Biochemistry (1988) 27:6008–6013; Keohavong and Thilly, Proc. Natl. Acad. Sci. U.S.A. (1989) 86:9253–9257; Cariello, Swenberg et al., Nucleic Acids Res. (1991) 19:4193–4198; Ling, Keohavong et al, supra; Lundberg, Shoemaker et al., Gene (1991) 108:1–6; Barnes, Proc. Natl. Acad. Sci. USA (1992) 91:2216–2220).

C. Conclusion

Amplification with the above HF system resulted in a 5-fold higher fidelity compared to amplification with the ADVANTAGE MIX under standard conditions. At the same time the amount of DNA after amplification of the plasmid used for the fidelity assay dropped about 3.5-fold. Compared to amplification with Taq polymerase, the fidelity was 17-fold higher with slightly higher DNA yield. The HF amplification system allowed amplifications of DNA fragments up to 2.5 kb from cDNA or genomic DNA templates (data not shown).

The HF system is useful for amplifications when high fidelity is needed such as in mutant detection or cloning of genes. It introduces per PCR cycle only 1 error in a million. A typical example would be the amplification of a 2000 bp gene in a PCR of 30 cycles. In this example, the HF system would introduce an average of only 0.06 mutations per 2000-bp fragment. Therefore, if individual fragments of this gene were cloned, 16 out of 17 clones would contain the wildtype sequence. This example indicates that the HF system allows cloning of wildtype sequences with a high probability and, therefore, reduces the requirement to confirm the DNA sequences of cloned fragments. Compared with PCR systems relying on proofreading polymerases it competes with regard to fidelity and provides increased levels of reliability and convenience.

It is evident from the above discussion and results that the subject methods and compositions provide for improved results in applications where PCR is performed. In particular, the subject methods provide for higher fidelity at greater efficiency than is available with presently available PCR methods.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

(i) a denaturation;
(ii) annealing; and
(iii) polymerization whereby a polymerase chain reaction is performed in which the error frequency rate does not exceed $1.3 \times 10^{-6}$ mutations per base pair per PCR cycle.

5. The method according to claim 4, wherein said reagent mixture comprises unequal concentrations of dNTPs.

6. The method according to claim 4, wherein said reagent mixture comprises a melting point reducing agent.

What is claimed is:

1. A method of performing a high fidelity polymerase chain reaction (PCR), said method comprising:
   (a) contacting a template DNA nucleic acid with a PCR reagent mixture that comprises both a Family A polymerase and a Family B polymerase and provides for an error frequency rate that does not exceed $1.3 \times 10^{-6}$ mutations per base pair per PCR cycle; and
   (b) performing a plurality of reaction cycles, wherein each cycle comprises:
      (i) denaturation;
      (ii) annealing; and
      (iii) polymerization;
   whereby a polymerase chain reaction is performed in which the error frequency rate does not exceed $1.3 \times 10^{-6}$ mutations per base pair per PCR cycle.

2. The method according to claim 1, wherein said reagent mixture further comprises unequal concentrations of dNTPs.

3. The method according to claim 1, wherein said reagent mixture further comprises a melting point reducing agent.

4. A method of performing a high fidelity polymerase chain reaction (PCR), said method comprising:
   (a) contacting a template nucleic acid with primer and a reagent mixture comprising at least one Family A and Family B polymerase and at least one of: unequal amounts of dNTPs and a melting point reducing agent, wherein said reagent mixture provides for an error frequency rate that does not exceed $1.3 \times 10^{-6}$ mutations per base pair per PCR cycle; and
   (b) performing a plurality of reaction cycles, wherein each cycle comprises:

7. The method according to claim 4, wherein said reagent mixture is further characterized by the presence of more Family A polymerase than Family B polymerase.

8. A method of performing a high fidelity polymerase chain reaction (PCR), said method comprising:
   (a) contacting a template DNA with primer and a reagent mixture that provides for an error frequency rate that does not exceed $1.3 \times 10^{-6}$ mutations per base pair per PCR cycle, wherein said reagent mixture comprises:
      (i) at least one Family A and Family B polymerase;
      (ii) unequal concentrations of dNTPs; and
      (iii) urea; and
   (b) performing a plurality of reaction cycles, wherein each cycle comprises:
      (i) denaturation;
      (ii) annealing; and
      (iii) polymerization;
   whereby a polymerase chain reaction is performed in which the error frequency rate does not exceed $1.3 \times 10^{-6}$ mutations per base pair per PCR cycle.

9. The method according to claim 8, wherein said reagent mixture comprises more Family A polymerase than Family B polymerase.

10. The method according to claim 9, wherein said Family A polymerase is selected from the group consisting of a Taq polymerase, a Tth polymerase, and homologues thereof.

11. The method according to claim 9, wherein said Family B polymerase is selected from the group consisting of a Vent polymerase, a Deep Vent polymerase, a Pfu polymerase and a Pwo polymerase.

12. The method according to claim 8, wherein said unequal concentrations of dNTPs are characterized by at least one of a greater amount of dATP and a lesser amount of dGTP with respect to the remaining dNTPs.

13. The method according to claim 8, wherein said urea is present in an amount ranging from about 20 to 500 mM.

14. The method according to claim 8, wherein said plurality of cycles comprises from about 5 to 40 cycles.

15. A method of performing a high fidelity polymerase chain reaction (PCR), said method comprising:
 (a) contacting a template DNA with primer and reagents to produce a reaction mixture that provides for an error frequency rate that does not exceed $1.3 \times 10^{-6}$ mutations per base pair per PCR cycle, wherein said reagents comprise:
  (i) a Family A polymerase and Deep Vent polymerase, wherein said Family A polymerase is present in an amount greater than said Deep Vent polymerase; and
  (ii) unequal concentrations of dNTPs, wherein said unequal concentrations of dNTPs are characterized by at least one of a greater amount of dATP and a lesser amount of dGTP with respect to the remaining dNTPs; and
 (b) performing from about 5 to 40 reaction cycles, wherein each cycle comprises:
  (i) denaturation;
  (ii) annealing; and
  (iii) polymerization;
 whereby a polymerase chain reaction is performed in which the error frequency rate does not exceed $1.3 \times 10^{-6}$ mutations per base pair per PCR cycle.

16. The method according to claim 15 wherein the pH of said reaction mixture ranges from about 6.0 to 9.5

17. The method according to claim 15, wherein said reaction mixture is characterized by having a magnesium ion concentration ranging from about 0.5 to 10 mM.

18. A reagent mixture for use in high fidelity polymerase chain reactions, said mixture comprising
 (a) at least one Family A polymerase;
 (b) at least one Family B polymerase; and
 (c) urea.

19. The reagent mixture according to claim 18, wherein said reagent mixture further comprises unequal concentration of dNTPs.

20. The reagent mixture according to claim 19, wherein said urea is present in an amount ranging from about 20 to 500 mM.

21. The reagent mixture according to claim 18, wherein said Family A polymerase is selected from the group consisting of a Taq polymerase and a Tth polymerase.

22. The reagent mixture according to claim 18, wherein said Family B polymerase is selected from the group consisting of a Vent polymerase, a Deep Vent polymerase, a Pfu polymerase and a Pwo polymerase.

23. A reagent mixture for use in high fidelity polymerase chain reactions, said mixture comprising:
 (a) a Family A polymerase and Deep Vent polymerase, wherein said Family A polymerase is present in amount greater than said Deep Vent polymerase;
 (b) unequal concentrations of dNTPS, wherein said unequal concentrations of dNTPs are characterized by at least one of a greater amount of dATP and a lesser amount of dGTP with respect to the remaining dNTPs.
 (c) urea in an amount ranging from about 20 to 500 mM.

24. A kit for use in performing high fidelity polymerase chain reactions, said kit comprising:
 (a) at least one Family A polymerase;
 (b) at least one Family B polymerase; and
 (c) urea.

25. The kit according to claim 24, wherein said Family A polymerase is selected from the group consisting of a Taq polymerase and a Tth polymerase.

26. The kit according to claim 24, wherein said Family B polymerase is selected from the group consisting of a Vent polymerase, a Deep Vent polymerase, a Pfu polymerase and a Pwo polymerase.

27. The kit according to claim 24, wherein said kit further comprises unequal concentrations of dNTPs.

28. The kit according to claim 24, wherein said urea is present in an amount ranging from about 20 to 500 mM.

29. A kit for use in high fidelity polymerase chain reactions, said kit comprising:
 (a) a Family A polymerase and Deep Vent polymerase, wherein said Family A polymerase is present in amount greater than said Deep Vent polymerase;
 (b) unequal concentrations of dNTPs, wherein said unequal concentrations of dNTPs are characterized by at least one of a greater amount of dATP and a lesser amount of dGTP with respect to the remaining dNTPs; and
 (c) urea in an amount ranging from about 20 to 500 mM.

* * * * *